(12) United States Patent
Hashimoto et al.

(10) Patent No.: US 11,717,366 B2
(45) Date of Patent: Aug. 8, 2023

(54) MEDICAL MANIPULATOR

(71) Applicants: KAWASAKI JUKOGYO KABUSHIKI KAISHA, Kobe (JP); MEDICAROID CORPORATION, Kobe (JP)

(72) Inventors: Yasuhiko Hashimoto, Kobe (JP); Toshiaki Yoshida, Kobe (JP); Kazunori Suga, Kobe (JP)

(73) Assignees: KAWASAKI JUKOGYO KABUSHIKI KAISHA, Kobe (JP); MEDICAROID CORPORATION, Kobe (JP)

(*) Notice: Subject to any disclaimer, the term of this patent is extended or adjusted under 35 U.S.C. 154(b) by 311 days.

(21) Appl. No.: 16/726,277

(22) Filed: Dec. 24, 2019

(65) Prior Publication Data

US 2020/0205920 A1 Jul. 2, 2020

(30) Foreign Application Priority Data

Dec. 26, 2018 (JP) ................................. 2018-243445
Dec. 12, 2019 (JP) ................................. 2019-224517

(51) Int. Cl.
*A61B 90/50* (2016.01)
*A61B 50/13* (2016.01)
(Continued)

(52) U.S. Cl.
CPC .............. *A61B 34/70* (2016.02); *A61B 34/37* (2016.02); *A61B 34/74* (2016.02); *A61B 50/13* (2016.02);
(Continued)

(58) Field of Classification Search
CPC combination set(s) only.
See application file for complete search history.

(56) References Cited

U.S. PATENT DOCUMENTS

2017/0079730 A1 3/2017 Azizian et al.
2017/0079731 A1* 3/2017 Griffiths ..................... B25J 9/02
(Continued)

FOREIGN PATENT DOCUMENTS

| JP | 2017-104452 A | 6/2017 |
|---|---|---|
| JP | 2017-513550 A | 6/2017 |
| JP | 2017-515524 A | 6/2017 |

*Primary Examiner* — Scott Luan
(74) *Attorney, Agent, or Firm* — Metrolex IP Law Group, PLLC

(57) ABSTRACT

A medical manipulator according to an embodiment may include an arm base including a first engagement portion and a manipulator arm including a distal end portion to support a surgical tool and a proximal end portion including a second engagement portion. One of the first and second engagement portions includes a shaft member and the other includes an engagement member engageable with the shaft member such that the engagement member engaged with the shaft member is rotatable with respect to the shaft member. The arm base includes a restriction portion to restrict rotation of the manipulator arm about the shaft member to which the engagement member is engaged. The proximal end portion of the manipulator arm is fixed to the restriction portion of the arm base with a fixing member in a state where restriction portion stops the rotation of the manipulator arm.

20 Claims, 11 Drawing Sheets

(51) Int. Cl.
 *A61B 34/00* (2016.01)
 *A61B 34/37* (2016.01)
 *A61B 34/30* (2016.01)
 *A61B 17/00* (2006.01)

(52) U.S. Cl.
 CPC .... *A61B 90/50* (2016.02); *A61B 2017/00477* (2013.01); *A61B 2017/00973* (2013.01); *A61B 2034/305* (2016.02)

(56) References Cited

U.S. PATENT DOCUMENTS

| | | | |
|---|---|---|---|
| 2017/0095300 A1* | 4/2017 | Devengenzo | H01R 13/6582 |
| 2017/0172676 A1 | 6/2017 | Itkowitz et al. | |
| 2018/0360550 A1 | 12/2018 | Nakanishi | |

\* cited by examiner

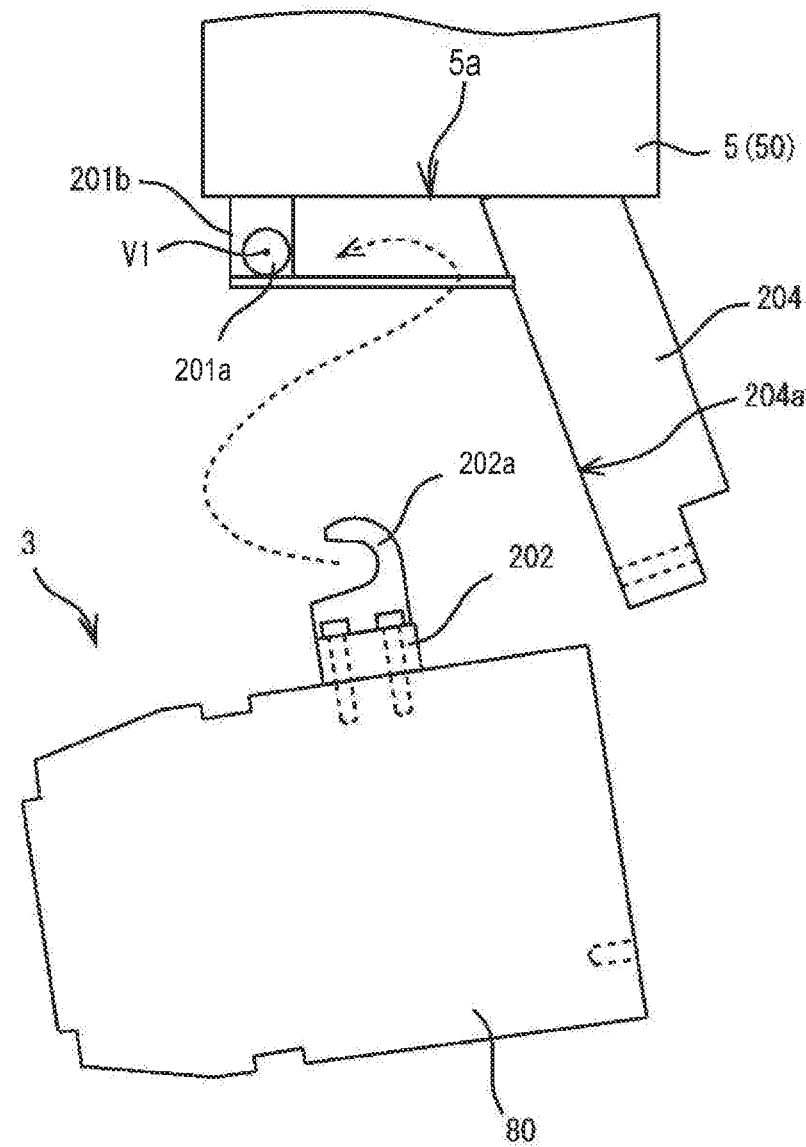

MEDICAL MANIPULATOR

CROSS REFERENCE TO RELATED APPLICATIONS

This application claims priority to Japanese Patent Application No. 2018-243445 filed on Dec. 26, 2018 and Japanese Patent Application No. 2019-224517 filed on Dec. 12, 2019, the entire contents of each of which are incorporated herein by reference.

BACKGROUND

The disclosure may relate to a medical manipulator.

There has been known a master-slave type surgical system that includes multiple manipulator arms and performs surgery by moving the manipulator arms based on operation of a surgeon (for example, see Documents 1 and 2).

In such a system, as described in Documents 1 and 2, proximal end portions of manipulator arms are attached to an arm base (or, also referred to as a platform) via setup links and setup joints, respectively. In other words, the manipulator arms are attached to the arm base via the setup links and setup joints, in such a manner that the manipulator arms are hung down from the arm base.

Document 3 discloses a mechanism that makes it easy to attach and detach manipulator arms to and from the setup links.

Document 3 discloses a configuration in which a connection end of a manipulator arm is connected with a connection end of a setup link, wherein one of the connection ends has a hook and the other of the connection ends has a slot to which the hook is inserted.

Document 1: Published Japanese Translation of PCT International Application No. 2017-515524

Document 2: Published Japanese Translation of PCT International Application No. 2017-513550

Document 3: U.S. Patent Application Publication No. 2017/0095300

However, Documents 1 to 3 do not disclose a configuration in which a manipulator arm is configured to be detachably attached to an arm base for convenience upon maintenances and/or replacements.

Further, Documents 1 to 3 do not disclose that a proximal end portion of the manipulator arm is easily and securely attached to the arm base with a simple configuration.

An object of an embodiment of the disclosure is to provide a medical manipulator that is capable of easily attaching and detaching a manipulator arm to and from an arm base.

A first aspect of one or more embodiments may be a medical manipulator that may include: an arm base including a first engagement portion; and a manipulator arm including a distal end portion including a tool support portion configured to support a surgical tool and a proximal end portion including a second engagement portion engageable with the first engagement portion. One of the first and second engagement portions includes a shaft member, and the other of the first and second engagement portion includes an engagement member that is engageable with the shaft member, such that in the state where the engagement member is engaged with the shaft member, the engagement member is rotatable with respect to the shaft member. The arm base includes a restriction portion to restrict rotation of the manipulator arm about the shaft member, in the state where the engagement member and the shaft member are engaged with each other. The proximal end portion of the manipulator arm is fixed to the restriction portion of the arm base with a fixing member in a state where restriction portion of the arm base restricts the rotation of the manipulator arm.

A second aspect of one or more embodiments may be a medical manipulator that may include: a manipulator arm including a distal end portion including a tool support portion configured to support a surgical tool; an arm base configured to hold the proximal end portion of the manipulator arm; a first engagement portion provided to the arm base; a second engagement portion provided to the proximal end portion of the manipulator arm; a shaft member provided to one of the first and second engagement portions and extending in a first axial direction; an engagement member provided to the other of the first and second engagement portions and engageable with the shaft member such that in the state where the engagement member is engaged with the shaft member, the engagement member is rotatable with respect to the shaft member; a restriction portion provided to the arm base and configured to come in contact with the proximal end portion of the manipulator arm to restrict rotation of the manipulator arm about the shaft member in the state where the engagement member is engaged with the shaft member; and a fixing member configured to fix the proximal end portion of the manipulator arm to the restriction portion.

A third aspect of one or more embodiments may be a method of attaching to an arm base a manipulator arm whose distal end portion includes a tool support portion configured to support a surgical tool. The method may include: engaging a second engagement portion provided to the proximal end portion of the manipulator arm to a first engagement portion of the arm base, wherein one of the first engagement portion and the second engagement portion is provided with a shaft member, and the other of the first engagement portion and the second engagement portion is provided with an engagement member engageable with the shaft member such that in a state where the engagement member is engaged with the shaft member, the engagement member is rotatable with respect to the shaft member; causing the manipulator arm to rotate about the shaft member due to the weight of the manipulator arm, to thereby stop the rotation of the manipulator arm in place by a restriction portion provided to the arm base; and fixing the proximal end portion of the manipulator arm to the restriction portion of the arm base using a fixing member.

According to the aspect described above, it may be possible to realize a configuration capable of easily attaching and detaching the manipulator arm to and from the arm base.

An object, characteristics, and advantages of the invention may be apparent from the detailed descriptions of the one or more embodiments below with reference to the accompanying drawings.

BRIEF DESCRIPTION OF DRAWINGS

FIGS. 7A to 7C are diagrams illustrating an example of a procedure of attaching the arm 3 to the arm base 5.

DETAILED DESCRIPTION

Figure 1:
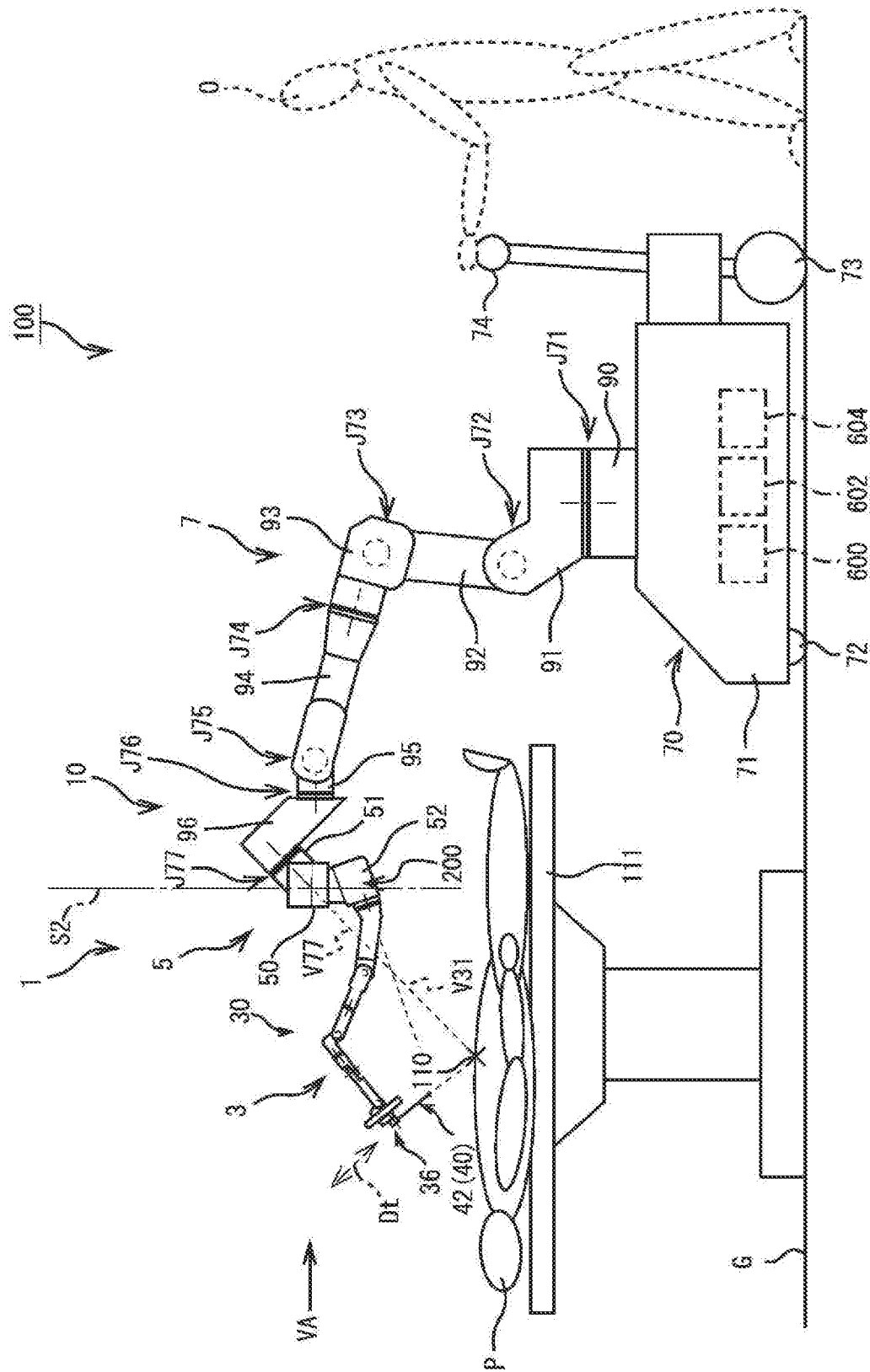
FIG. 1 is a diagram illustrating a schematic view of an overall configuration of a surgical system including a support mechanism according to one or more embodiments.

Descriptions are provided hereinbelow for one or more embodiments based on the drawings. The invention is not limited to the one or more embodiments. In the respective drawings referenced herein, the same or equivalent constituents are designated by the same reference numerals and duplicate explanation concerning the same or equivalent constituents is omitted. All of the drawings are provided to illustrate the respective examples only.

FIG. 1 is a diagram illustrating a schematic view of an overall configuration of a surgical system in which a support mechanism is provided according to one or more embodiments. A surgical system 100 is a system for a surgeon such as a doctor to perform endoscopic surgery on a patient P with a patient-side system 1, like robotic-assistant surgery and robotic telesurgery. FIG. 1 illustrates a state in which a positioner 7, an arm base 5, and manipulator arms 3 are set in a predetermined preparation position that is determined before procedure (details are described later). In FIG. 1, the ratio of the size of the illustrated manipulator arms 3 to the positioner 7 is different from the actual ratio.

The surgical system 100 includes the patient-side system 1 and an operation apparatus 2 serving as an instruction apparatus (see FIG. 4 described later) for controlling the manipulator arms 3 of the patient-side system 1. The operation apparatus 2 is disposed apart from the patient-side system 1, and the patient-side system 1 is remotely controlled by the operation apparatus 2 during procedure. The surgeon inputs an action to be executed by the patient-side system 1 to the operation apparatus 2, and the operation apparatus 2 transmits the action instruction to the patient-side system 1. The patient-side system 1 receives the action instruction transmitted from the operation apparatus 2. Based on the action instruction, the patient-side system 1 operates a tool such as an elongated surgical tool 40 held by the patient-side system 1.

The operation apparatus 2 is an apparatus constructing an interface between the surgical system 100 and the surgeon so as to control the patient-side system 1. The operation apparatus 2 is disposed nearby or away from an operating table 111 (a surgical bed) in a surgery room or disposed outside of the surgery room. Although it is not illustrated, the operation apparatus 2 includes operation input units such as an operation manipulator arm and an operation pedal for the surgeon to input the action instruction, and a monitor that displays an image captured by an endoscope assembly (not illustrated) as the surgical tool 40 attached to the patient-side system 1. The surgeon operates the operation input units to input the action instruction to the operation apparatus 2 while visually checking an affected area (a surgery site 110) through the monitor. The action instruction inputted to the operation apparatus 2 is transmitted to the later-described controller 600 of the patient-side system 1 through wired or wireless communications.

The patient-side system 1 constructs an interface between the surgical system 100 and the patient P. In the surgery room, the patient-side system 1 is disposed nearby the operating table 111 on which the patient P is laid. Inside of the surgery room is sterilized to be a sterile field.

The patient-side system 1 includes the positioner 7, the arm base (platform) 5 attached to the distal end portion of the positioner 7, and the patient-side manipulator arms (hereinafter, simply referred to as "arms 3") detachably attached to the arm base 5. The positioner 7 is a device extending from a base to connect the base with the arm base 5. In this embodiment, the positioner 7 is formed as a multi-axis robot. The positioner 7 can move the position of the arm base 5 three-dimensionally with respect to a movable wagon 70, which is the base. The arm 3 and the arm base 5 are covered with a sterile drape(s) (not-illustrated) and shielded from the sterile field in the surgery room.

The distal end portion of each of the arms 3 is configured as a tool holding part (a holder 36) that can hold the elongated surgical tool 40. The distal end portion of one of the arms 3 holds the endoscope assembly (not illustrated). The distal end portion of the rest of the arms 3 detachably holds an instrument 42. Hereinafter, the arm 3 to which the endoscope assembly is attached may be referred to as a "camera arm," and the arm 3 to which the instrument 42 is attached may be referred to as an "instrument arm." The patient-side system 1 in this embodiment includes four arms 3 including one camera arm and three instrument arms.

In the above-described patient-side system 1, the arm base 5 serves as a "hub" that is a base of the arms 3. In this embodiment, the positioner 7 and the arm base 5 form a manipulator arm support body 10 that movably supports the arms 3. Note that the positioner 7 may not be a multi-axis robot. For example, the positioner 7 may be a liner rail to support the arm base 5, a lifting and lowering device to support he arm base 5, or a bracket attached to a ceiling or a wall to support the arm base 5. The base to which the positioner 7 is connected is not limited to a movable configuration such as a wagon 70 or a wheeled base. For example, the base may be a wall or floor of the surgery room or a stationary member that is fixed to the wall or the floor.

In the above-described patient-side system 1, the elements from the positioner 7 to the endoscope assembly or the instrument 42 are connected in series. In this disclosure, in each of the series of elements, an end portion closer to the positioner 7 (more specifically, an end portion closer to a base 90 that is a connection portion between the positioner 7 and the wagon 70) is referred to as a "proximal end portion," and an end portion on the opposite side is referred to as a "distal end portion."

The wagon 70, the positioner 7, the arm base 5, and the manipulator arms 3 are described in detail below.

As illustrated in FIG. 1, the wagon 70, serving as a wheeled base, includes a wagon body 71, front wheels 72 and rear wheels 73, and a handle 74. The front wheels 72 and the rear wheels 73 are rotatably attached to the wagon body 71, and the wagon body 71 is thus configured to be movable. The rear wheels 73 are configured to be turnable about a rotational axis of the handle 74, and this makes it possible to change a traveling direction of the wagon body 71 with the surgeon or a surgical assistant O grasping and turning the handle 74 about the rotational axis.

Operation of the patient-side system 1 is controlled by the controller 600. The controller 600 is formed of a computer such as a microcontroller, for example. The controller 600 and a storage 602 in which a control program and various kinds of data used for the operation control are stored are housed inside the wagon body 71. The wagon body 71 is also provided with an operation unit 604, which is mainly for setting and inputting the position and orientation of the positioner 7, the arm base 5, and the arms 3 before procedure (the later-described preparation orientation). The operation unit 604 is formed of a touch panel and the like, for example.

The positioner 7 includes the base 90 attached to the wagon body 71 and positioner link portions subsequently connected with each other from the base 90 toward the distal end portion. With one positioner link portion rotatably connected to another positioner link unit subsequently, the positioner 7 forms multiple joint portions. The positioner link portions include a first link 91 to a sixth link 96. The joint portions include a first joint J71 to a seventh joint J77. Each of the joint portions in this embodiment is formed of a joint having a rotation axis; however, at least one or more of the joint portions may be formed of a direct-acting joint.

More specifically, the proximal end portion of the first link 91 is connected to the distal end portion of the base 90 with the first joint J71 as a roll joint arranged therebetween. The proximal end portion of the second link 92 is connected to the distal end portion of the first link 91 with the second joint J72 as a pivotal (pitch) joint arranged therebetween. The proximal end portion of the third link 93 is connected to the distal end portion of the second link 92 with the third joint J73 as a pivotal joint arranged therebetween. The proximal end portion of the fourth link 94 is connected to the distal end portion of the third link 93 with the fourth joint J74 as a roll joint arranged therebetween. The proximal end portion of the fifth link 95 is connected to the distal end portion of the fourth link 94 with the fifth joint J75 as a pivotal joint arranged therebetween. The proximal end portion of the sixth link 96 is connected to the distal end portion of the fifth link 95 with the sixth joint J76 as a roll joint arranged therebetween. A positioner attachment portion 51 of the arm base 5 is connected to the distal end portion of the sixth link 96 with the seventh joint J77 as a roll joint arranged therebetween. Thus, the positioner 7 is formed as a multi-axis joint (seven-axis joint) arm having the multi-degree of freedom (seven degrees of freedom).

As described above, in the sixth link 96 as a positioner link portion attached to the positioner attachment portion 51 of the arm base 5, both the sixth joint J76 as a joint portion on the base end side and the seventh joint J77 as a joint portion on the distal end side are formed as the roll joints. In addition, the rotation axis of the sixth joint J76 is relatively inclined with respect to the rotation axis of the seventh joint J77. More specifically, the rotation axis of the sixth joint J76 is inclined with respect to the longitudinal direction of the sixth link 96, while the rotation axis of the seventh joint J77 is orthogonal to the longitudinal direction of the sixth link 96. An extension of the rotation axis of the sixth joint J76 and an extension of the rotation axis of the seventh joint J77 cross each other. That is, the surface of revolution of the sixth joint J76 is inclined with respect to the surface of revolution of the seventh joint J77.

The arm base 5 includes an arm base body 50, the positioner attachment portion 51 that is attached to the top (on the base end side) of the arm base body 50 with the distal end portion of the positioner 7 attached to the positioner attachment portion 51, and at least one arm attachment portion that is attached to the bottom (on the distal end side) of the arm base body 50 with the proximal end portions of the arms 3 attached to the arm attachment portion. Note that the arm attachment portion is covered with a cover 52. The arm attachment portion comprises a later described first engagement portion 201 and a restriction portion 204. The arm base 5 is configured to be relatively rotatable with respect to the distal end portion of the positioner 7 (the sixth link 96) about the rotation axis of the seventh joint J77, serving as an arm base rotation axis V77. In this embodiment, multiple (four) arm attachment portions are provided in accordance with the multiple (four) arms 3. Bases 80 of the arms 3 are respectively secured to the arm attachment portions. Thus, the proximal end portion of each arm 3 (a later-described first link 81) is configured to be relatively rotatable about a rotation axis of a later-described first joint J31, serving as an arm proximal end rotation axis V31. A more specific configuration of the arm base 5 is described later.

Figure 2:
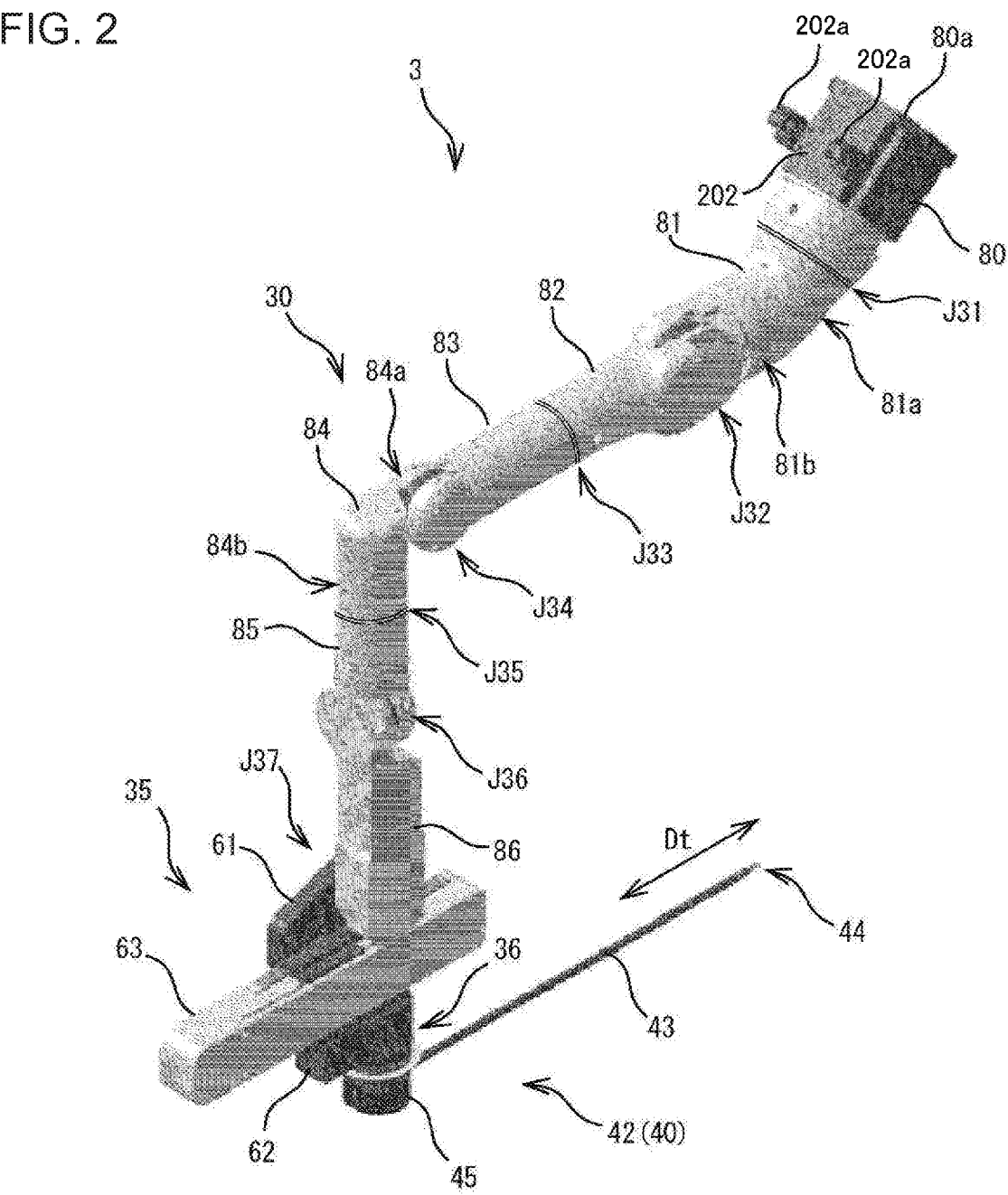
FIG. 2 is a diagram illustrating a schematic view of an overall configuration of a manipulator arm of the surgical system illustrated in FIG. 1.

FIG. 2 is a schematic view of an overall configuration of the manipulator arm of the surgical system illustrated in FIG. 1. FIG. 2 illustrates a schematic configuration of a single arm 3 to which the instrument 42 is attached, the single arm 3 being out of the multiple arms 3 provided to the patient-side system 1. In this embodiment, the arms 3 provided to the patient-side system 1 have the same or similar configurations; however, at least one of the arms 3 may have a different configuration from the other arms (for example, may have different degrees of freedom, or the like). As illustrated in FIG. 2, the arm 3 includes an arm body 30 and a translation unit 35 connected to the distal end portion of the arm body 30. The arm 3 is formed such that the distal end portion thereof is three-dimensionally movable with respect to the corresponding proximal end portion. The distal end portion of the arm 3 is provided with the holder (the tool holding unit) 36 that can hold the elongated surgical tool 40 (the instrument 42 or the endoscope assembly). In this embodiment, the holder 36 is provided to the translation unit 35.

The instrument 42 includes a drive unit 45 provided to the proximal end portion, an end effector (procedure tool) 44 provided to the distal end portion, and an elongated shaft 43 connecting the drive unit 45 and the end effector 44. The drive unit 45, the shaft 43, and the end effector 44 are arranged along an axis direction Dt or a longitudinal direction of the instrument 42. The end effector 44 of the instrument 42 is selected from a group including a tool having a movable joint (for example, pair of forceps, pair of scissors, grasper, needle holder, micro dissector, staple applier, tacker, suction and irrigation tool, snare wire, clip applier, and so on) and a tool having no joints (for example, cutting blade, ablation probe, irrigation device, catheter, suction orifice, and so on). In this disclosure, an "elongated surgical tool" includes both the endoscope assembly and the instruments.

When the arm 3 is the instrument arm, the holder 36 detachably holds the instrument 42. The shaft 43 of the instrument 42 held by the holder 36 extends along the axis direction Dt. On the other hand, when the arm 3 is the camera arm, the holder 36 detachably holds the endoscope assembly. In this case, the holder 36 provided to the camera arm may have a different shape or configuration from that of the holder 36 provided to the instrument arm. In addition, since it is rare to make replacement of the endoscope assembly during surgery, the endoscope assembly may be secured to the camera arm.

The arm 3 is configured to be attachable to and detachable from the arm base 5. The arm 3 has resistances for irrigation processing and sterile processing, including water resistance, heat resistance, and chemical resistance. There are various ways for the sterile processing of the arm 3. For example, autoclave sterilization, EOG sterilization, chemical sterilization with an antiseptic, and so on may be selectively used.

The arm body 30 includes a base 80 detachably attached to the arm base 5 and arm link portions sequentially connected with each other from the base 80 toward the distal end portion. With one arm link portion rotatably connected to another arm link portion sequentially, the arm 3 forms multiple joint portions. The arm link portions include the first link 81 to a seventh link 87. The joint portions include the first joint J31 to a seventh joint J37. Each of the joint portions in this embodiment is formed of a rotation joint having a rotation axis; however, at least a part of the joint portions may be formed of a direct-acting joint.

More specifically, the proximal end portion of the first link 81 is connected to the distal end portion of the base 80 with the first joint J31 as a roll joint arranged therebetween. The proximal end portion of the second link 82 is connected to the distal end portion of the first link 81 with the second joint J32 as a pivotal (pitch) joint arranged therebetween. The proximal end portion of the third link 83 is connected to the distal end portion of the second link 82 with the third joint J33 as a roll joint arranged therebetween. The proximal end portion of the fourth link 84 is connected to the distal end portion of the third link 83 with the fourth joint J34 as a pivotal joint arranged therebetween. The proximal end portion of the fifth link 85 is connected to the distal end portion of the fourth link 84 with the fifth joint J35 as a roll joint arranged therebetween. The proximal end portion of the sixth link 86 is connected to the distal end portion of the fifth link 85 with the sixth joint J36 as a pivotal joint arranged therebetween. The proximal end portion of the translation unit 35 is connected to the distal end portion of the sixth link 86 with the seventh joint J37 as a pivotal joint arranged therebetween. Thus, the arm 3 is formed as a multi-axis joint (seven-axis joint) arm having the multi-degree of freedom (seven degrees of freedom). Consequently, the arm 3 can change the overall orientation thereof without changing the position and orientation of the distal end portion of the arm 3.

In this embodiment, the first link 81 has a bending shape between the joints J31 and J32 next to each other. In other words, the first link 81 is formed such that the rotation axis of the first joint J31 and the rotation axis of the second joint J32 do not cross each other. That is, the first link 81 includes a first portion 81a and a second portion 81b. The first portion 81a extends in a predetermined first direction (a rotation axis direction of the first joint J31) from the first joint J31 on the base end side. The second portion 81b extends in a second direction crossing the extending direction of the first portion 81a (the second direction also being a direction orthogonal to the second joint J32) from the distal end portion of the first portion 81a to be connected to the second joint J32 on the distal end side. An angle formed by the first direction and the second direction at the first link 81 is, for example, 120 degrees or more and 160 degrees or less (for example, 140 degrees). The first portion 81a and the second portion 81b are smoothly connected with each other. This makes it possible to easily arrange wires (not illustrated) such as electric wirings in the arm link portions although one of the arm link portions has the bending shape.

In addition, the fourth link 84 has a bending shape between the joints J34 and J35 next to each other. In other words, the fourth link 84 is formed such that the rotation axis of the fourth joint J34 and the rotation axis of the fifth joint J35 do not cross each other. That is, the fourth link 84 includes a first portion 84a and a second portion 84b. The first portion 84a extends in a first direction (a direction orthogonal to both the rotation axis of the fourth joint J34 and the rotation axis of the fifth joint J35) from the fourth joint J34 on the base end side. The second portion 84b extends in a second direction crossing the extending direction of the first portion 84a (a rotation axis direction of the fifth joint J35) from the distal end portion of the first portion 84a to be connected to the fifth joint J35 on the distal end side. An angle formed by the first direction and the second direction at the fourth link 84 is, for example, 70 degrees or more and 110 degrees or less (for example, 90 degrees). The first portion 84a and the second portion 84b are smoothly connected with each other.

Figure 3:
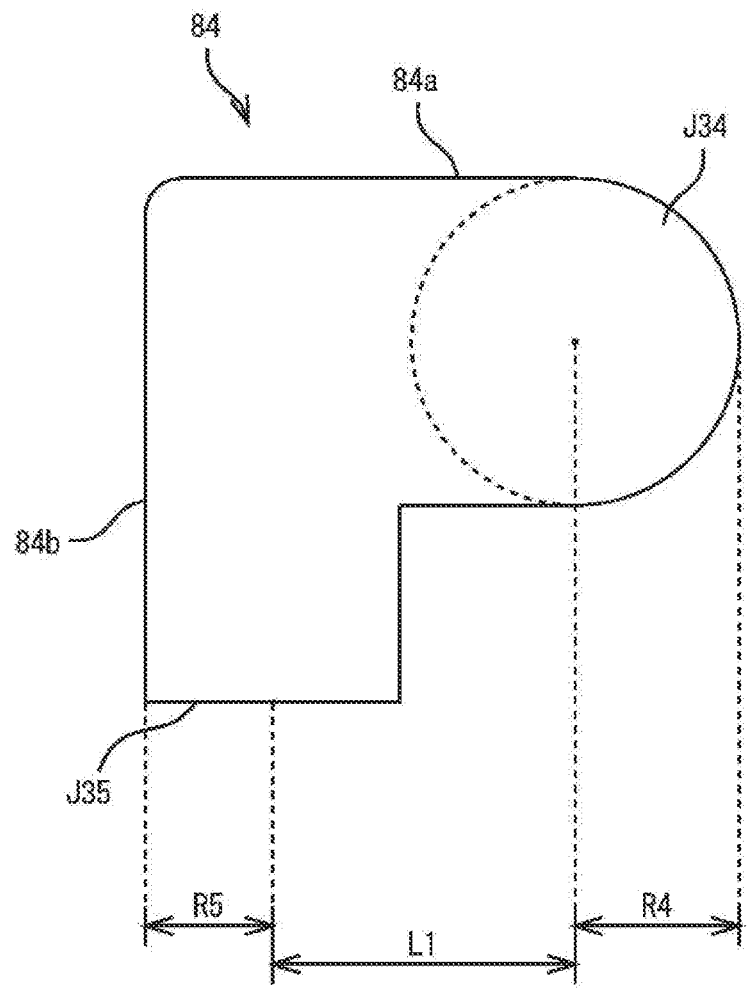
FIG. 3 is a diagram illustrating a side view schematically illustrating an example of a fourth link illustrated in FIG. 2.

Specifically, the fourth link 84 is formed to have the link length shorter than those of the other joint portions. FIG. 3 is a side view schematically illustrating an example of the fourth link 84 illustrated in FIG. 2. As illustrated in FIG. 3, for example, the fourth link 84 is formed such that a length L1 in the first direction between the rotation axis of the fourth joint J34 and the rotation axis of the fifth joint J35 is no more than four times, or more preferably no more than three times, of a radius R4 of the fourth joint J34 or a radius R5 of the fifth joint J35. The radius R4 of the fourth joint J34 is defined as a distance between the rotation axis of the fourth joint J34 and a position of the proximal end portion of the fourth link 84 in the first direction. The radius R5 of the fifth joint J35 is defined as a distance between the rotation axis of the fifth joint J35 and a position of the distal end portion of the fourth link 84 in the first direction. The fourth link 84 is formed such that the length L1 is no more than two times of the sum of the radius R4 of the fourth joint J34 and the radius R5 of the fifth joint J35. More preferably, the above-described length L1 is shorter than a length obtained by adding the radius R5 of the fifth joint J35, which is the shorter one between the radius R4 of the fourth joint J34 and the radius R5 of the fifth joint J35, to the sum of the radius R4 of the fourth joint J34 and the radius R5 of the fifth joint J35.

The other links 82, 83, 85, and 86 are each formed in a straight line shape between the joint portions next to each other. In other words, the other links 82, 83, 85, and 86 are formed such that the rotation axes of the joint portions next to each other cross each other.

The arm link portions are formed such that one arm link portion has the smaller area of a cross section orthogonal to the longitudinal direction than that of the other arm link portion (or the base 80) connected on the base end side of the one arm link portion. Accordingly, the arm 3 is formed to be gradually narrower from the proximal end portion toward the distal end portion. In addition, the joints J32, J34, and J36 as the pivotal joints are formed as follows. The distal end portion of each of the arm link portions 81, 83, and 85 on the base end side is positioned on one side in the rotation axis direction relative to a middle portion in the rotation axis direction in the corresponding joint portion. Meanwhile, the proximal end portion of each of the arm link portions 82, 84, and 86 on the distal end side is positioned on the other side in the rotation axis direction relative to the middle portion in the rotation axis direction in the corresponding joint portion, such that the proximal end portions of the arm link portions 82, 84, and 86 face the distal end portions of the arm link portions 81, 83, and 85, respectively. That is, these joints J32, J34, and J36 are formed by the halved joint.

Besides, a width of each joint portion in the rotation axis direction is shorter than a diameter (the maximum dimension) of a cross section of a portion closer to the proximal end portion of corresponding one of the arm link portions 81, 83, and 85 on the base end side, the cross section being orthogonal to the longitudinal direction. The width of the joint portion is a distance between an outer end portion in the rotation axis direction of the distal end portion of corresponding one of the arm link portions 81, 83, and 85 on the base end side and an outer end portion in the rotation axis direction of the proximal end portion of corresponding one of the arm link portions 82, 84, and 86 on the distal end side.

As described above, each joint portion and the arm link portion on the distal end side of the joint portion is formed narrower than the arm link portion on the base end side. This makes it possible to increase a moving range of the arm 3 (a range in which the arm 3 does not interfere with the other) in a work space that becomes narrower as the arm 3 comes closer to the surgery site 110 of the patient P.

An outer shell of the arm body 30 is formed of a member having heat resistance and chemical resistance, such as mainly stainless. An opening portion of the arm body 30 such as an inspection hole is covered with a resin cover. With the cover formed of a member such as resin, it is possible to achieve weight reduction of a portion that does not contribute the strength of the arm 3. Consequently, it is possible to reduce the accidental impact caused when the cover falls off or when the arm 3 hits another arm 3 or the surgical assistant O, for example. The outer shell itself of the arm body 30 may include a portion formed of a resin member. A connection portion between the links is provided with sealing (not illustrated) to provide water resistance. The sealing has the heat resistance for autoclaved sterilization and the chemical resistance for antiseptic. In the connection portion between the links, an end portion of one link is inserted into an end portion of the other link to be connected with the one link, and the sealing is arranged so as to fill the space between the end portions of the links. Thus, the sealing is hidden from external appearance. In this way, entering of water, chemical liquid, and vapor through the space between the sealing and the link is suppressed.

The translation unit 35 is a mechanism that translationally moves the instrument 42 attached to the holder 36 in the extending direction of the shaft 43 by translationally moving the holder 36 attached to the distal end portion of the translation unit 35 in the axis direction Dt.

The translation unit 35 includes a base end side link 61 that is connected to the distal end portion of the sixth link 86 of the arm body 30 with the seventh joint J37 as a pivotal joint arranged therebetween, a distal end side link 62, a connection link 63 that moves between the base end side link 61 and the distal end side link 62 in an interlocking manner, and an interlocking mechanism (not illustrated). The seventh joint J37 extends in a direction orthogonal to the axis direction Dt. A drive source of the translation unit 35 is provided to the base end side link 61. The connection link 63 extends along the axis direction Dt.

In the translation unit 35, the interlocking mechanism allows changings of relative positions of the base end side link 61 and the connection link 63 in the axis direction Dt and relative positions of the connection link 63 and the distal end side link 62 in the axis direction Dt, and accordingly it is possible to change a position of the instrument 42 attached to the holder 36 provided to the distal end side link 62 in the axis direction Dt with respect to the base end side link 61. A publicly known link mechanism can be employed as the interlocking mechanism. The interlocking mechanism may have a configuration using a pulley and a timing belt or may be a mechanism including a gear train, for example.

Figure 4:
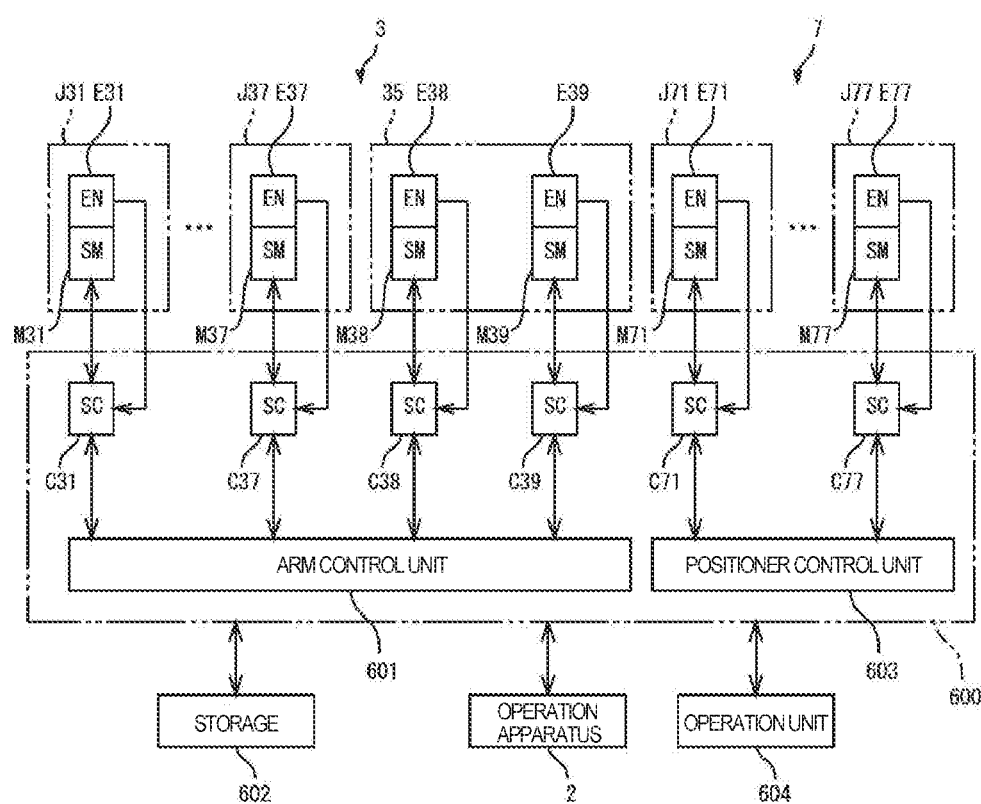
FIG. 4 is a block diagram illustrating a view of a schematic configuration of a control system of the manipulator arm of the surgical system illustrated in FIG. 1.

FIG. 4 is a block diagram illustrating a schematic configuration of a control system of the manipulator arm of the surgical system illustrated in FIG. 1. The arm body 30 having the above-described configuration is provided with driving servomotors (indicated as SM in FIG. 4) M31 to M37, encoders (indicated as EN in FIG. 4) E31 to E37 detecting rotation angles of the servomotors M31 to M37, and reduction drives (not illustrated) reducing the outputs of the servomotors M31 to M37 to increase the torque, with each corresponding to the joints J31 to J37 of the arm 3. Likewise, the positioner 7 is provided with driving servomotors M71 to M77, encoders E71 to E77 detecting rotation angles of the servomotors M71 to M77, and reduction drives (not illustrated) reducing the outputs of the servomotors M71 to M77 to increase the torque, with each corresponding to the joints J71 to J77 of the positioner 7.

Among the joints J31 to J37 and J71 to J77 in FIG. 4, the control systems of the first joint J31 and the seventh joint J37 of the arm 3 and the control systems of the first joint J71 and the seventh joint J77 of the positioner 7 are illustrated as a representative, and the control systems of the other joints J33 to J36 and J72 to J76 are omitted. In addition, the translation unit 35 is provided with a servomotor M38 for the translational movement, a servomotor M39 for rotating a rotating body provided in the drive unit 45 of the surgical instrument 42, encoders E38 and E39 detecting rotation angles of the servomotors M38 and M39, and reduction drives (not illustrated) reducing the outputs of the servomotors M38 and M39 to increase the torque.

The encoders E31 to E39 and E71 to E77 are provided as an example of rotation position detection units for detecting the rotation positions (the rotation angles) of the servomotors M31 to M39 and M71 to M77. Rotation position detection units such as resolvers may be used instead of the encoders E31 to E39 and E71 to E77. The above-described elements of the drive systems of the arm 3 and wirings and control units for the elements are made of high-temperature resistant materials and have the heat resistance for sterile processing.

The controller 600 includes an arm control unit 601 that controls the movements of the arms 3 based on the action instructions and a positioner control unit 603 that controls the movement of the positioner 7. Servo-control units C31 to C39 are electrically connected to the arm control unit 601, and the servomotors M31 to M39 are electrically connected to the arm control unit 601 via not-illustrated amplifier circuits and the like. Likewise, servo-control units C71 to C77 are electrically connected to the positioner control unit 603, and the servomotors M71 to M79 are electrically connected to the positioner control unit 603 via not-illustrated amplifier circuits and the like.

In the above-described configuration, based on the action instruction inputted to the operation apparatus 2 during procedure, a position and orientation instruction of the distal end portion of the arm 3 is inputted to the arm control unit 601. Based on the position and orientation instruction, the arm control unit 601 generates position instruction values for the servomotors M31 to M39 and outputs the thus-generated position instruction values to the corresponding servo-control units C31 to C39. The servo-control units C31 to C39 receive the position instruction values, and then generate drive instruction values (torque instruction values) based on the rotation angles detected by the encoders E31 to E39 and the received position instruction values and output the thus-generated drive instruction values. The amplifier circuits receive the drive instruction values, and then supply drive currents corresponding to the received drive instruction values to the servomotors M31 to M39. As described above, the servomotors M31 to M39 are servo-controlled such that the distal end portion of the arm 3 is set at the position and orientation corresponding to the position and orientation instruction. Further, based on the action instruction inputted to the operation unit 604 before the surgery, a position and orientation instruction of the distal end portion of the positioner 7 is inputted to the positioner control unit 603. Like the arm control unit 601, the positioner control unit 603 controls the position and orientation of the positioner 7 based on the position and orientation instruction.

The controller 600 includes a storage 602 that can read out data to the arm control unit 601. The storage 602 stores in advance surgery information that is inputted through the operation apparatus 2. The surgery information includes information that indicates what types of the arms 3 are to be used together in surgery.

The storage 602 stores information such as the length of a surgical tool (the endoscope assembly or the instrument) held by the distal end portion of the arm 3 along the axis direction Dt. This allows the arm control unit 601 to grasp the position of the distal end portion of the surgical tool held by the distal end portion of the arm 3 based on the position and orientation instruction of the distal end portion of the arm 3.

In addition, the storage 602 stores in advance the preparation position for the positioner 7, the arm base 5, and the arms 3 (for example, positions and orientations of the elements 7, 5, and 3 illustrated in FIG. 1) that is determined before procedure. The storage 602 can store the preparation positions in accordance with a detail (type) of surgery, a surgery site, and so on. In addition, the storage 602 stores in advance a predetermined storing position. The predetermined storing position is set as the position and orientation in which the positioner 7 and the arms 3 are folded as much as possible so as to prevent the arms 3 and the like from coming into contact with a wall of the surgery room or other surgical equipment and the like while moving by the wagon 70.

Based on an action instruction for operation (predetermined control input) such as setting of the preparation position inputted to the operation unit 604, the positioner control unit 603 controls the positioner 7, the arm base 5, and the arms 3 to move to the preparation position stored in the storage 602.

In procedure using the patient-side system 1 having the above-described configuration, first, the surgical assistant O (or the surgeon him/herself) moves the patient-side system 1 closer to the operating table 111 using the wagon 70. In this process, the positioner 7, the arm base 5, and the arms 3 are set at the predetermined storing position (not illustrated) set with respect to the wagon 70.

After the patient-side system 1 is moved, the surgical assistant O uses the operation unit 604 to selectively input the preparation position in accordance with the surgery type for the patient P. In this way, the positioner control unit 603 reads the information on the corresponding preparation position from the storage 602 and controls the operations of the positioner 7, the arm base 5, and the arms 3 such that these elements are set in the preparation position.

It is also possible to use the operation unit 604 to independently adjust the positions of the positioner 7, the arm base 5, and the arms 3 from the preparation position. Additionally, the surgical assistant O also can independently move the arms 3 from the preparation position by grasping the arms 3 and the like. With such preliminary operations, the positions of the positioner 7, the arm base 5, and the arms 3 are determined such that the sleeve (cannula sleeve) placed on the body surface of the patient P as the surgery site 110 and the surgical tools 40 attached to the arms 3 have an initial position relationship.

In an embodiment, the controller 600 does not receive the operation outputted from the operation apparatus 2 until the patient-side system 1 (the positioner 7, the arm base 5, and the arms 3) is set from the storing position to the preparation position. After the patient-side system 1 is set in the preparation position, the controller 600 can start to receive the operation outputted from the operation apparatus 2. During the procedure after the patient-side system 1 is set in the preparation position, the controller 600 properly changes the positions and orientations of the surgical tools 40 by controlling the operations of the arms 3 in response to the action instruction from the operation apparatus 2 while, in principle, keeping the positioner 7 and the arm base 5 still.

As described above, the preparation position illustrated in FIG. 1 is set as a position before procedure, in which the arm base 5 and the operating table 111 or the patient P have a predetermined position relationship. In this preparation position, the arm base rotation axis V77 (described later) in the positioner attachment portion 51 of the arm base 5 is inclined with respect to both a horizontal plane (a first plane S1) and a vertical plane (a second plane S2) including the longitudinal direction (a first direction D1) of the arm base 5 and perpendicular to the horizontal plane, with the arm base 5 positioned such that the longitudinal direction of the arm base 5 is parallel to the horizontal plane (the first plane S1). In order to easily achieve the above-described preparation position, the arm base 5 of this embodiment have the following configuration.

Figure 5A:
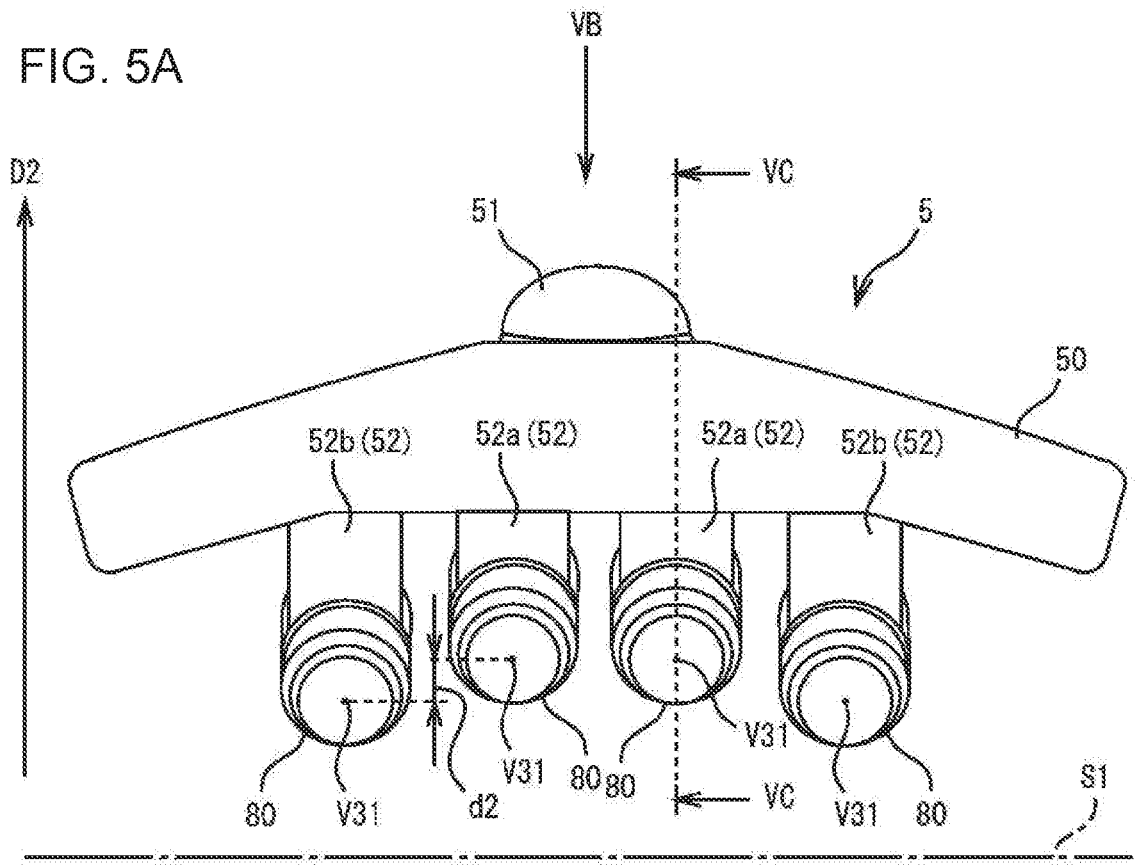
FIGS. 5A to 5C are diagrams illustrating schematic views of a configuration of the arm base in the surgical system illustrated in FIG. 1.
Figure 5B:
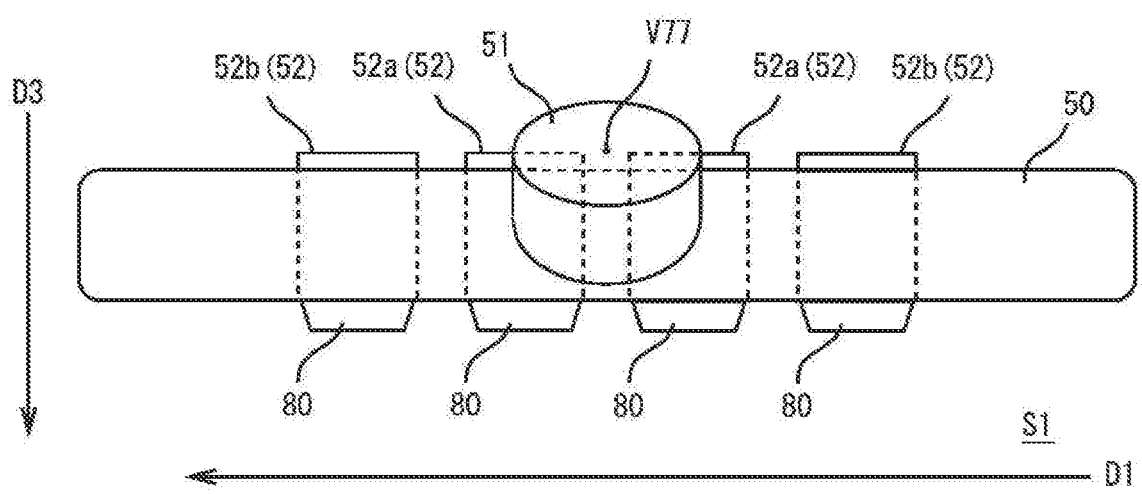
Figure 5C:
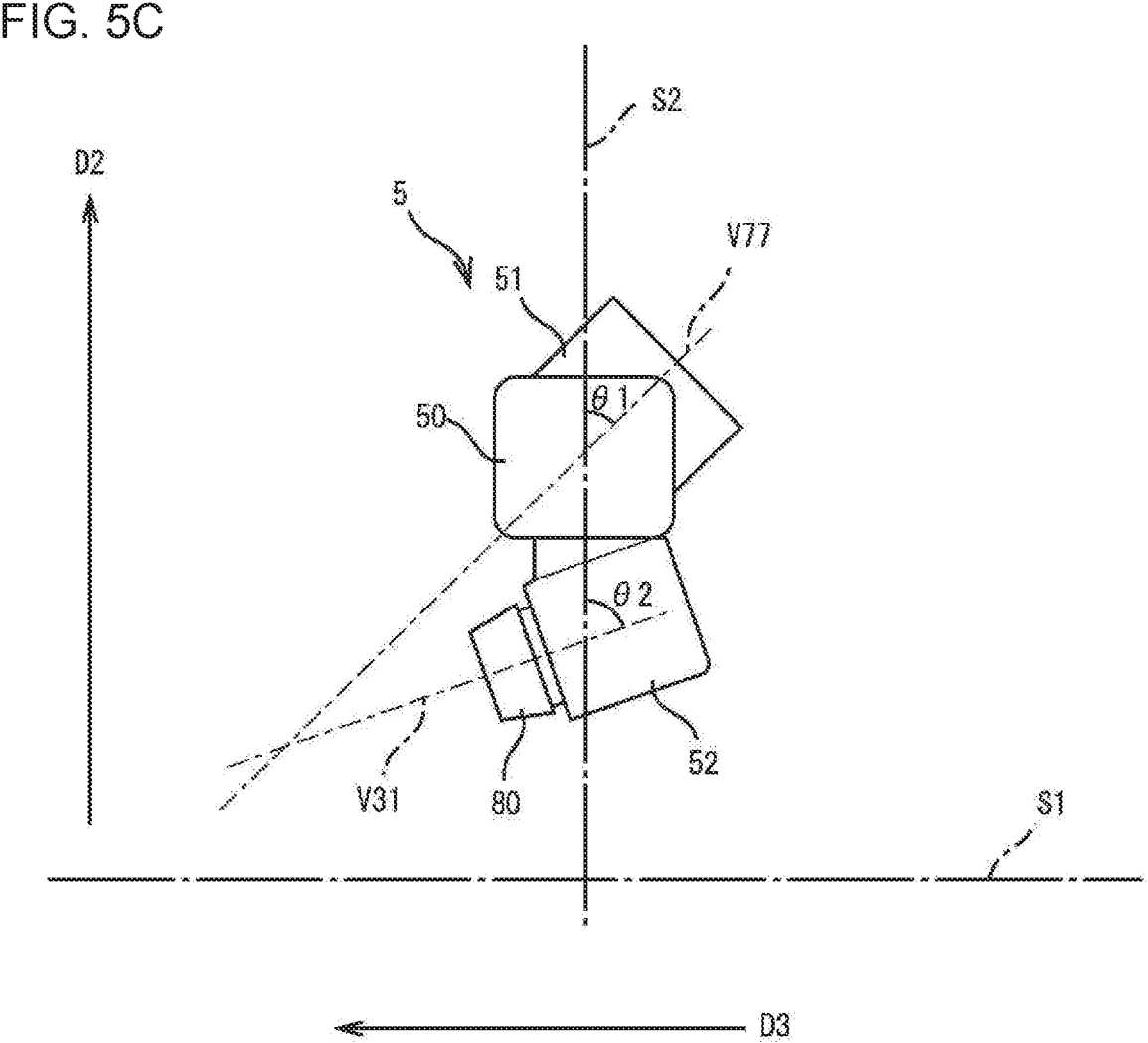

FIGS. 5A to 5C are schematic views illustrating a configuration of the arm base in the surgical system illustrated in FIG. 1. FIG. 5A is a front view as seen from the front side (from the VA direction in FIG. 1) in the preparation position illustrated in FIG. 1, FIG. 5B is a top view as seen from the VB direction illustrated in FIG. 5A, and FIG. 5C is a cross-sectional view taken along the VC-VC indicated in FIG. 5A.

The covers 52 to cover the arm attachment portions are formed as follows. As illustrated in FIG. 5B, in a plan view of the first plane S1, the proximal end portions of the arms 3 (the bases 80) are aligned in the predetermined first direction D1 that is included in the first plane S1. In this embodiment, the first plane S1 is a virtual plane parallel to a floor surface (a horizontal plane) G with the arm base 5 set in the preparation position (FIG. 1). That is, the arm attachment portions are aligned in the first direction D1 (a depth direction with respect to the paper surface of FIG. 1) when the arm base 5 set in the preparation position is seen from above.

In addition, in this embodiment, the position of the proximal end portion of at least one of the arms 3 in the second direction (the vertical direction) D2 perpendicular to the first plane S1 is configured to be different from the positions of the proximal end portions of the other arms 3 in the second direction D2. In FIGS. 5A and 5B, among the covers 52 to cover the aligned four arm attachment portions, covers for two arm attachment portions on the inner side are covers 52a for inner arm attachment portions while covers for the other two arm attachment portions on the outer side are covers 52b for outer arm attachment portions. In this embodiment, the position of the base 80 of the arm 3 attached to each of the inner arm attachment portions (in FIG. 5A, the position is based on the arm proximal end rotation axis V31 as the rotation axis of the first joint J31) is higher by a predetermined distance d2 than the position of the base 80 of the arm 3 attached to each of the outer arm attachment portions.

As illustrated in FIG. 5C, the positioner attachment portion 51 extends from the top of the arm base body 50 in the arm base rotation axis V77 direction. The arm base rotation axis V77 is configured to be inclined with respect to the virtual second plane S2 including the first and second directions D1 and D2.

In addition, the arm attachment portions (later-described first engagement portion 201 and restriction portion 204) are fixed to the arm base body 50 such that the attachment directions of the arms 3 are set in the same direction.

Moreover, as illustrated in FIG. 5C, the arm attachment portions are configured to hold the arms 3 such that the arm proximal end rotation axis V31 of each arm 3 is inclined with respect to the second plane S2. In this case, an angle of inclination θ1 of the arm base rotation axis V77 with respect to the second plane S2 is smaller than an angle of inclination θ2 of the arm proximal end rotation axis V31 with respect to the second plane S2. In other words, the angle formed by the arm attachment direction of the arm attachment portion is closer to horizontal than the angle formed by the direction of the arm base rotation axis V77. Thus, an extension of the arm base rotation axis V77 and an extension of the arm proximal end rotation axis V31 cross each other. For example, the angle of inclination θ1 of the arm base rotation axis V77 with respect to the second plane S2 is around 45° (an angle of inclination of the arm base rotation axis V77 with respect to the first plane S1 is also around 45°), while the angle of inclination θ2 of the arm proximal end rotation axis V31 with respect to the second plane S2 is around 60° (an angle of inclination of the arm proximal end rotation axis V31 with respect to the first plane S1 is around 30°).

Figure 6A:
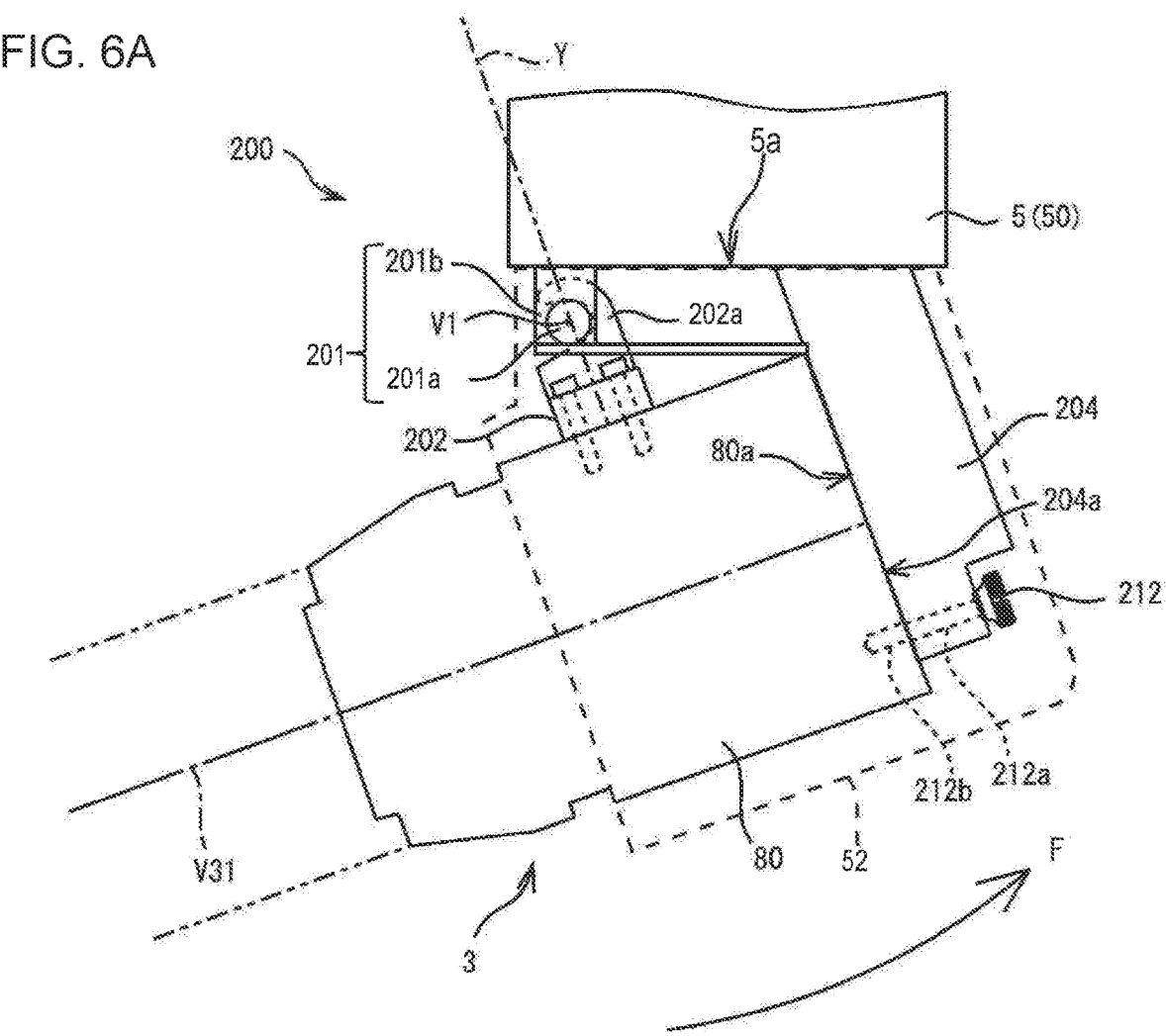
FIGS. 6A and 6B are diagrams illustrating schematic views of a configuration of a support mechanism for the arm.
Figure 6B:
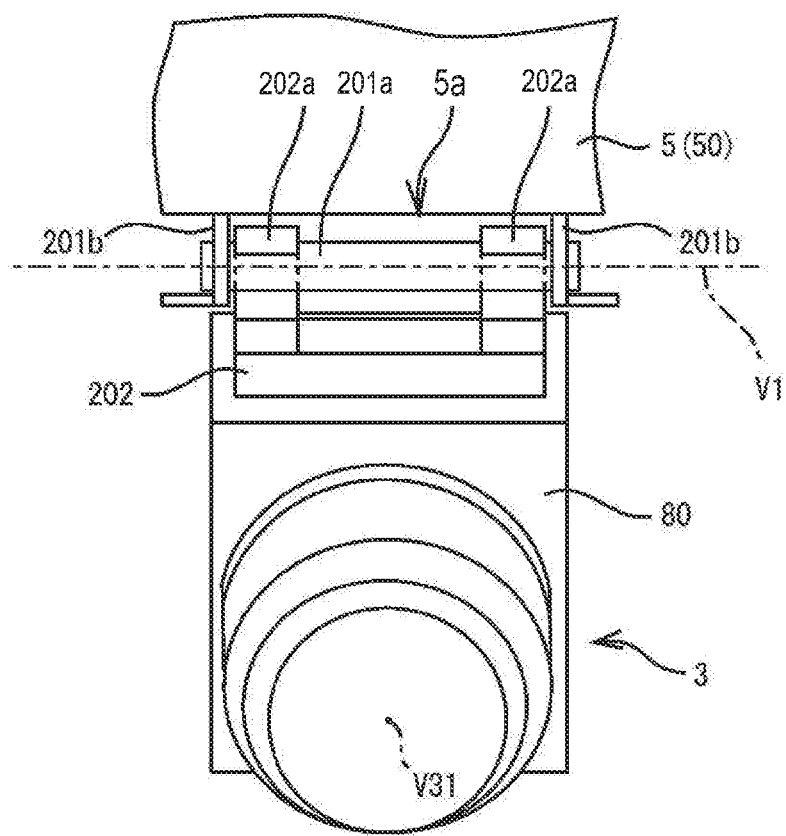

FIGS. 6A and 6B are diagrams illustrating schematic views of the configuration of the support mechanism for the arm. Note that FIG. 6A illustrates a state where the cover 52 is removed in FIG. 5C and FIG. 6B illustrates a front view of the support mechanism as seen from the front side (in a direction VA in FIG. 1) in the preparation position, such as being illustrated in FIG. 1. Note that in FIGS. 6A and 6B, of the arm 3, only the base 80 is illustrated and the rest is omitted. The support mechanism 200 is configured to detachably support the arm 3 to the arm base 5. The support mechanism 200 includes the first engagement portion 201 and the restriction portion 204 fixed to the arm base body 50 of the arm base 5 and a second engagement portion 202 detachably attached to the proximal end portion of the arm 3 (the base 80).

The first engagement portion 201 includes a shaft member 201a extending in a first axis V1 direction along the longitudinal direction D1 of the arm base 5. The first engagement portion 201 is formed with an attachment surface 5a parallel to the first axis V1, such that the attachment surface 5a of the first engagement portion 201 is to be attached to the arm base 5. The first engagement portion 201 also includes a pair of shaft support portions 201b extending in a downward direction (a direction away from the arm base 5) from the attachment surface 5a. The shaft member 201a is held by the pair of shaft support portions 201b. The shaft member 201a is, for example, formed of a metal column member or the like. The shaft member 201a is provided at one end (front end) of the attachment surface 5a in the front-rear direction (a direction orthogonal to the longitudinal direction D1 and parallel to the attachment surface 5a). The shaft member 201a is supported by the pair of shaft support portions 201b. The attachment surface 5a is oriented horizontally in the preparation position such as being illustrated in FIG. 1.

The arm base 5 includes the restriction portion 204 extending downwardly from the other end portion (the rear end portion) of the attachment surface 5a in the front-rear direction. The restriction portion 204 includes a restriction surface 204a parallel to the first axis V1 and inclined with respect to the attachment surface 5a. Specifically, the restriction surface 204a is configured to extend backwardly toward a lower end portion from an upper end portion thereof. An arm attachment portion of the arm base 5 is composed of the first engagement portion 201 and the restriction portion 204.

The second engagement portion 202 includes an engagement member 202a which is engageable with the shaft member 201a. In the state where the engagement member 202a is engaged with the shaft member 201a, the engagement member 202a is rotatable about the first axis V1. The second engagement portion 202 extends in a longitudinal direction of the base 80 of the arm 3 (arm proximal end rotation axis V31 direction) and in a direction Y orthogonal to the longitudinal direction D1. The engagement member 202a is provided at a tip end portion or a distal end portion of the second engagement portion 202. The engagement member 202a is formed in a hook shape. The hook serving as the engagement member 202a includes an opening whose diameter is larger than the diameter of the shaft member 201a such that the opening is opened in a direction orthogonal to the extending direction of the second engagement portion 202 (toward the distal end of the arm 3).

The second engagement portion 202 is configured such that the engagement member 202a thereof is attached at a position away, in the longitudinal direction of the base 80 (the arm proximal end rotational axis V31 direction), from the proximal end portion of the base 80 (the contact surface 80a of the proximal end portion to the restriction surface 204a) toward the distal end portion of the base 80 by a predetermined distance. The engagement member 202a includes engagement portions provided both widthwise ends of the second engagement portion 202. That is, the second engagement portion 202 includes two engagement members 202a.

The restriction portion 204 is configured to restrict the rotation of the arm 3 about the first axis V1 in the state where the engagement member 202a is engaged with the shaft member 201a (in the state where the second engagement portion 202 is mounted to the arm 3) by the restriction surface 204a thereof coming in contact with the proximal end portion of the base 80 (the contact surface 80a). The base 80 serving as the proximal end portion of the arm 3 includes the contact surface 80a orthogonal to the longitudinal axis of the base 80.

Note that, for power supply from the arm base 5 to the arm 3 and signal transmission between the arm base 5 and the arm 3, an electrical connection between the arm base 5 to the arm 3 can be made by means of connection of a first connector provided at an end of a first electrical wiring extending from the proximal end portion of the arm 3 and a second connector provided at an end of a second electrical wiring extending from the arm base 5. Accordingly, electrical connectors for the electrical connection between the arm base 5 and the arm 3 are not provided at the restriction surface 204a of the restriction portion 204 and the contact surface 80a at the proximal end portion of the arm 3.

In a case where connectors are provided at the restriction surface 204a and the contact surface 80a respectively, it is required to connect such connectors to each other while rotating the arm 3 about the first axis V1. In such a case, a force may be applied to the connectors in directions other than a direction for connecting the connectors, which may cause a deformation of the connectors or a poor electrical connection. In this embodiment, the electrical connection between the arm base 5 and the arm 3 can be done separately from the support mechanism 200 for the arm 3. This does not require to electrically connect the connectors to each other while rotating the arm 3, which brings about a stable electrical connection.

Figure 7A:
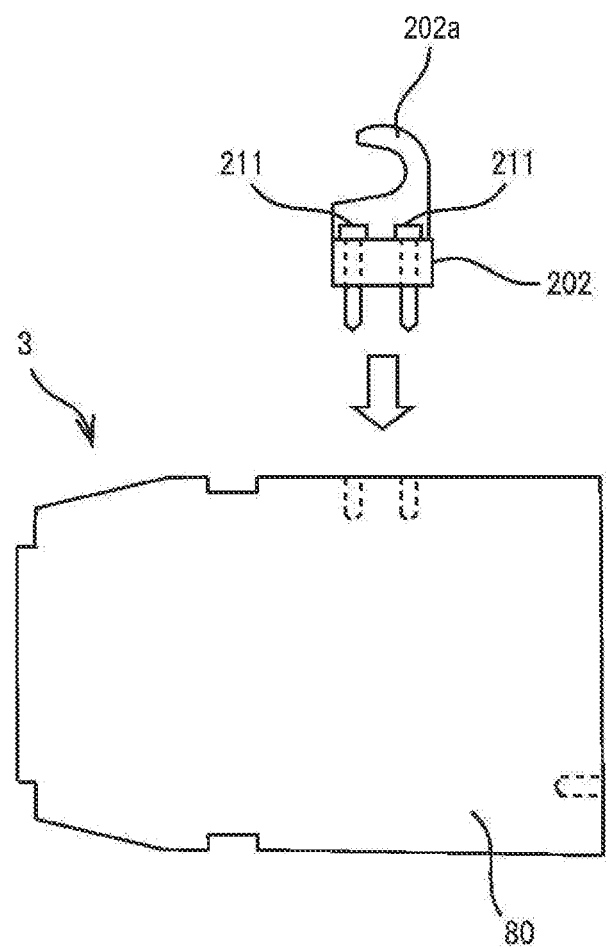
Figure 7C:
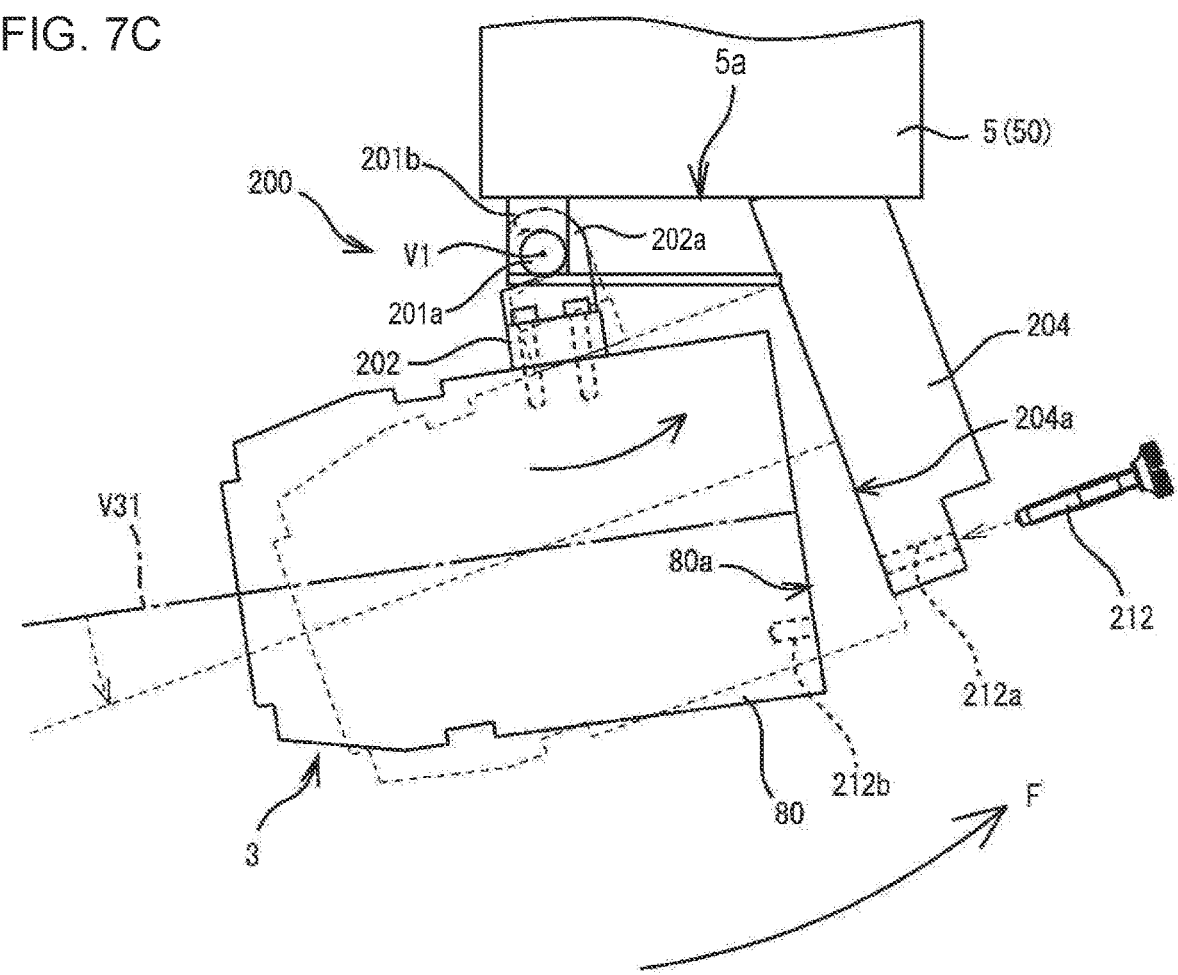

A procedure of mounting the arm 3 to the arm base 5 according to the above described configuration is described below. FIGS. 7A to 7C are diagrams illustrating an example of the procedure of mounting the arm 3 to the arm base 5 according to one or more embodiments. The first engagement portion 201 is fixed to the arm base 5 in advance. First, as illustrated in FIG. 7A, the second engagement portion 202 provided with the engagement member 202a is attached to the base 80 of the arm 3 by means of predetermined fastener members 211 such as screws or the like.

Next, as illustrated in FIG. 7B, the shaft member 201a provided in the first engagement portion 201 is engaged with the engagement member 202a attached to the arm 3 via the second engagement portion 202. In this embodiment, the hook-shaped engagement member 202a is hooked to the column portion of the shaft member 201a, so as to be engaged with the column portion of the shaft member 201a. In the state where the engagement member 202a is engaged with the shaft member 201a, the engagement member 202a is relatively rotatable about the first axis V1. Specifically, an engagement surface of the engagement member 202a to the shaft member 201a is formed in a circular arc shape along a circumference of the shaft member 201a. Thus, in the state where the engagement member 202a is engaged with the shaft member 201a, the engagement is not easily released. In other words, the engagement member 202a is smoothly rotated about the shaft member 201a. With this, the arm 3 is kept being hung (hanging state) from the arm base 5.

As described above, not illustrated in FIGS. 6A and 6B, plural arm link portions are connected to the distal end portion of the base 80 of the arm 3. Therefore, as illustrated in FIG. 7C, the engagement member 202a is provided at a position closer to the proximal end in the longitudinal direction of the arm 3 than the center of gravity of the arm 3 in the longitudinal direction thereof. Accordingly, the arm 3 having the engagement member 202a engaged with the shaft member 201a receives a biasing force F, due to the weight of the arm 3, that biases the arm 3 to rotate about the first axis V1 in a direction to decrease the inclination angle of the longitudinal direction of the arm 3 with respect to the vertical direction In other words, the arm 3 receives the biasing force F, due to the weight of the arm 3, that lifts up the proximal end portion of the arm 3 upwardly. The restriction portion 204 is configured to restrict the rotation of the arm 3 about the first axis V1 due to the weight of the arm 3. As described above, the restriction portion 204 includes the restriction surface 204a which extends backwardly as it goes from the upper portion toward the lower portion thereof. Therefore, as illustrated in FIG. 6A, the proximal end portion of the arm 3 (the contact surface 80a) is kept in contact in with the restriction surface 204a due to the weight of the arm 3. In this state, the longitudinal direction of the base 80 is inclined with respect to the vertical direction.

As described above, because the restriction portion 204 is in contact with the proximal end portion of the arm 3, the arm 3 is positioned with respect to the arm base 5. With this, by simply attaching the arm 3 to the arm base 5, the arm 3 can be positioned in place with respect to the arm base 5.

In the state where the proximal end portion of the arm 3 is in contact with the restriction surface 204a of the restriction portion 204, the proximal end portion of the arm 3 is fixed to the restriction portion 204 through fastening members 212 such as screws or the like. For example, the restriction portion 204 is formed with through holes 212a extending through the restriction surface 204a at two positions along the widthwise direction, and the proximal end portion of the arm 3 (the contact surface) is formed with at the corresponding positions with screw holes 212b. The through holes 212a are provided at the positions in the vicinity of the lower end of the restriction portion 204. As described above, the contact between the proximal end portion of the arm 3 and the restriction portion 204 is maintained by the biasing force F due to the weight of the arm 3, an operator can perform operation of fastening the proximal end portion of the arm 3 to the restriction portion 204, without touching or holding the arm 3.

As illustrated in FIG. 6A, the support mechanism 200 includes the cover 52 that converse the shaft member 201a, the engagement member 202a, and the restriction portion 204 in an integrated manner in the state where the proximal end portion of the arm 3 is in contact with the restriction portion 204. The cover 52 is, for example, formed of a resin, a stainless steel, or the like. The cover 52 is configured to cover the entire of the first engagement portion 201 and a part of the proximal end portion of the arm 3 (more than the half of the base 80) in the integrated manner. Note that the cover 52 is attached after the proximal end portion of the arm 3 is fastened to the restriction portion 204.

With the above described configuration, in the state where the engagement member 202a is engaged with the shaft member 201a, the rotational movements of the arm 3 about the first axis V1 is restricted or stopped by the restriction portion 204 provided at the arm base 5. With this, upon attaching the arm 3 to the arm base 5, the operation of only engaging the engagement member 202a to the shaft member 201a extending in the first axis V1 direction makes the arm 3 supported by the arm base 5. Further, in the state where the engagement member 202a is engaged with the shaft member 201a, the engagement member 202a is relatively rotatable about the first axis V1. Thus, in the state where the engagement member 202a is engaged with the shaft member 201a, the engagement is not easily released. Thus, the attachment/detachment of the arm 3 with respect to the arm base 5 can be easily realized while preventing the arm 3 from coming off in the engagement state.

The engagement member 202a is attached to the arm 3 through the second engagement portion 202, which is detachably attached to the arm 3. That is, the second engagement portion 202 functions as a bracket. Accordingly, already-existing arms can be used as the arm 3, which can maintain or improve the versatility of the arm 3. Further, the shaft member 201a, the engagement member 202a, and the restriction portion 204 are all covered with the cover 52 in the state where the arm 3 is attached to the arm base 5. Accordingly, it prevents the engagement section from being exposed to the outside.

Further, the second engagement portion 202 extends in the direction Y orthogonal to both the longitudinal direction D1 of the arm base 5 and the longitudinal direction of the base 80 and the distal end portion of the second engagement portion 202 is provided with the engagement member 202a. This makes it easy to bias the arm 3 toward the restriction portion 204 using the weight of the arm 3. Further, the restriction portion 204 includes the restriction surface 204a that is parallel to the first axis V1 and inclined with respect to the attachment surface 5a. Accordingly, in the state where the arm 3 is attached to the arm base 5, the arm 3 can be arranged to extend obliquely downward. Therefore, the arm base 5 and the positioner 7 can be placed at a position different from that of the surgery site 110 in the horizontal direction. This can prevent giving a patient O oppressive feeling.

Further, the restriction portion 204 restricts or stops the rotation of the arm 3 about the first axis V1 due to the weight of the arm 3. Accordingly, in the state where the engagement member 202a is engaged with the shaft member 201a, the arm 3 is positioned where the arm 3 is to be fixed, without the operator rotating the arm 3 about the first axis V1. This can improve the workability for attaching the arm 3 and can effectively prevent the arm 3 from falling off.

Therefore, the arm 3 is configured to be suitable for a manipulator arm applied to the surgical system 100.

According to the above descriptions, many improvements and modifications of the above one or more embodiments are apparent to the person skilled in the art. Thus, the above descriptions should be construed as only an example, and the above descriptions are provided for teaching one or more aspects for executing the invention to the person skilled in the art. It is possible to practically change the details of the configuration and/or function of the above described one or more embodiments without departing from the spirit of the invention.

For example, in the above-described one or embodiments, the shaft member 201a is provided to the first engagement portion 201 fixed to the arm base 5, and the engagement member 202a is provided to the second engagement portion 202 detachably attached to the proximal end portion of the arm 3. However, in an embodiment, the engagement member 202a may be provided to the first engagement portion 201, and the shaft member 201a may be provided to the second engagement portion 202.

In the above-described one or embodiments, two of the engagement members 202a are provided. However, in an embodiment, the number of the engagement members 202a may be one and may be three or more. For example, in the case where only one engagement member 202a is provided, the length (width) of the engagement member 202a in the first axis V1 direction may be set to a length smaller than a distance between the pair of shaft support portions 101b by a predetermined allowance distance. Note that in the case to fix by means of the fastening members 212, the length (width) of the engagement member 202a in the first axis V1 direction is not limited as long as the length is shorter than the distance between the pair of shaft support portion 101 and the strength to support the arm 3 is enough.

Further, the shape of the engagement member 202a is not limited to the above described hook shape and may employ various shapes. For example, the engagement member 202a may have an annular shape (hole shape) and the shaft member 201a may have a projected shape extending in the first axis V1 direction. In such a case, the projected shaft member 201a is inserted in the annular engagement member 202a in the first axis V1 direction to engage with each other, such that the engagement member 202a is rotatable about the first axis V1 with respect to the shaft member 201a.

In each of the arms 3 and/or the positioners 7, the numbers of the joints and the links (the number of the degrees of the freedom) and the shapes of the joints and the links are not limited to the above described one or more embodiments and various aspects can be employed therefor.

In the above described one or more embodiments, the support mechanism 200 is applied for attaching the arm 3 to the arm base 5 of the surgical system 100. However, the support mechanism 200 can be applied to a system other than the surgical system 100.

The configurations described above is useful to realize a structure that can facilitate attachment and detachment of a manipulator arm to and from an arm base.

The invention claimed is:

1. A medical manipulator comprising:
an arm base including an attachment surface from which a first engagement portion and a restriction portion are projected; and
a manipulator arm including a distal end portion including a tool support portion configured to support a surgical tool, a proximal end portion including a second engagement portion, and plural links provided between the distal end portion and the proximal end portion and including a first link rotatably connected to the proximal end portion via a roll joint,
wherein one of the first and second engagement portions includes a shaft member extending an axial direction thereof parallel to the attachment surface,
the other of the first and second engagement portions includes an engagement member that is engageable with the shaft member, such that in a state where the engagement member is engaged with the shaft member, the engagement member is rotatable with respect to the shaft member,
the restriction portion of the arm base is formed with a restriction surface configured, in the state where the engagement member and the shaft member are engaged with each other, to come in contact with the proximal end portion of the manipulator arm to restrict rotation of the manipulator arm about the shaft member, wherein the restriction surface is parallel to the axial direction of the shaft member and is inclined with respect to the attachment surface of the arm base, and
the proximal end portion of the manipulator arm is fixed to the restriction portion of the arm base with a fixing member that extends through the restriction portion to the proximal end portion of the manipulator arm in a state where the restriction surface of the restriction portion of the arm base is in contact with the proximal end portion of the manipulator arm, such that an axis of the proximal end portion of the manipulator arm parallel to a first rotational axis of the roll joint is inclined with respect to the attachment surface of the arm base.

2. The medical manipulator according to claim 1, wherein the second engagement portion is projected from the proximal end portion of the manipulator arm, and a distal end portion of the second engagement portion includes one of the shaft member and the engagement member.

3. The medical manipulator according to claim 1, wherein the engagement member is formed in a hook shape.

4. The medical manipulator according to claim 1, wherein the restriction portion is configured to come in contact with the proximal end portion of the manipulator arm to restrict the rotation of the manipulator arm about the shaft member due to the weight of the manipulator arm.

5. The medical manipulator according to claim 1, wherein the restriction portion is configured to come in contact with the proximal end portion of the manipulator arm to position the manipulator arm with respect to the arm base.

6. The medical manipulator according to claim 1, wherein the proximal end portion of the manipulator arm is provided with a first connector and the arm base is provided with a second connector, such that a connection of the first connector and the second connector causes an electrical connection between the manipulator arm and the arm base, and the arm base is provided with the second connector at a position other than the restriction surface of the restriction portion with which the proximal end portion of the manipulator arm comes in contact.

7. The medical manipulator according to claim 1, wherein the manipulator arm is provided with a cover configured to cover the first engagement portion, the second engagement portion, and the restriction portion in an integrated manner in a state where the proximal end portion of the manipulator arm is in contact with the restriction portion.

8. The medical manipulator according to claim 1, further comprising
a positioner supporting the arm base through a second roll joint having a second rotational axis of the arm base and configured to move the arm base; and
a wheeled base to which the positioner is provided.

9. The medical manipulator according to claim 8, wherein the positioner comprises a multi-axis robot.

10. The medical manipulator according to claim 1, further comprising:
a second manipulator arm including a second distal end portion including a second tool support portion configured to support a second surgical tool, a second proximal end portion including a fourth engagement portion, and plural links provided between the second distal end portion and the second proximal end portion and including a second link rotatably connected to the second proximal end portion via a roll joint,
wherein the arm base comprises a third engagement portion projected from the attachment surface,
one of the third and fourth engagement portions includes a second shaft member extending an axial direction thereof parallel to the attachment surface, and
the other of the third and fourth engagement portions includes a second engagement member that is engageable with the second shaft member, such that in a state where the second engagement member is engaged with the second shaft member, the second engagement member is rotatable with respect to the second shaft member.

11. The medical manipulator according to claim 1, wherein
the restriction surface is a flat surface inclined with respect to the attachment surface, and
the flat restriction surface is configured to come in surface contact with a flat contact surface of the proximal end portion of the manipulator arm parallel to the first rotational axis of the roll joint, to restrict the rotation of the manipulator arm about the shaft member.

12. A medical manipulator comprising:
a manipulator arm including a distal end portion including a tool support portion configured to support a surgical tool, a proximal end portion, and plural links provided between the distal end portion and the proximal end portion and including a first link rotatably connected to the proximal end portion via a roll joint;
an arm base configured to hold the proximal end portion of the manipulator arm;
a first engagement portion projected from an attachment surface of the arm base;
a second engagement portion provided to the proximal end portion of the manipulator arm;
a shaft member provided to one of the first and second engagement portions and extending in a first axial direction;
an engagement member provided to the other of the first and second engagement portions and engageable with the shaft member such that in a state where the engagement member is engaged with the shaft member, the engagement member is rotatable with respect to the shaft member;
a restriction portion projected from the attachment surface of the arm base and including a restriction surface configured to come in contact with the proximal end portion of the manipulator arm to restrict rotation of the manipulator arm about the shaft member in the state where the engagement member is engaged with the shaft member, wherein the restriction surface is parallel to the first axial direction of the shaft member and is inclined with respect to the attachment surface of the arm base; and
a fixing member extending through the restriction portion to the proximal end portion of the manipulator arm and configured to fix the proximal end portion of the manipulator arm to the restriction portion in a state where the restriction surface is in contact with the proximal end portion of the manipulator arm, such that an axis of the proximal end portion of the manipulator arm parallel to a first rotational axis of the roll joint is inclined with respect to the attachment surface of the arm base.

13. The medical manipulator according to claim 12, wherein
the engagement member is formed in a hook shape.

14. The medical manipulator according to claim 12, wherein
the restriction portion is configured to restrict the rotation of the manipulator arm about the shaft member due to the weight of the manipulator arm.

15. The medical manipulator according to claim 12, further comprising:
a positioner supporting the arm base through a second roll joint having a second rotational axis of the arm base and configured to move the arm base; and
a wheeled base to which the positioner is provided.

16. The medical manipulator according to claim 15, wherein the positioner comprises a multi-axis robot.

17. A method of attaching to an arm base a manipulator arm whose distal end portion includes a tool support portion configured to support a surgical tool, the method comprising:
engaging a second engagement portion provided to a proximal end portion of the manipulator arm to a first engagement portion projected from an attachment surface of the arm base, wherein one of the first engagement portion and the second engagement portion is provided with a shaft member, and the other of the first engagement portion and the second engagement portion is provided with an engagement member engageable with the shaft member such that in a state where the engagement member is engaged with the shaft member, the engagement member is rotatable with respect to the shaft member;
causing the manipulator arm to rotate about the shaft member due to the weight of the manipulator arm, to thereby stop rotation of the manipulator arm in place by a restriction surface of a restriction portion projected from the attachment surface of the arm base, wherein the restriction surface of the arm base is parallel to an axial direction of the shaft member and is inclined with respect to the attachment surface of the arm base; and fixing the proximal end portion of the manipulator arm to the restriction portion of the arm base using a fixing member that extends through the restriction portion to the proximal end portion of the manipulator arm in a state where the restriction surface is in contact with the proximal end portion of the manipulator arm, such that an axis of the proximal end portion of the manipulator arm is inclined with respect to the attachment surface of the arm base.

18. The method according to claim 17, wherein the engagement member is formed in a hook shape.

19. The method according to claim 17, further comprising a positioner comprising a multi-axis robot configured to move the arm base; and a wheeled base to which the positioner is provided.

20. The method according to claim 19, further comprising covering the first engagement portion, the second engagement portion, and the restriction portion with a cover.

\* \* \* \* \*